(12) United States Patent
Konishi et al.

(10) Patent No.: US 9,375,506 B2
(45) Date of Patent: Jun. 28, 2016

(54) ABSORBENT ARTICLE

(75) Inventors: Takayoshi Konishi, Kanonji (JP); Masaki Yoshida, Kanonji (JP); Noritomo Kameda, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 191 days.

(21) Appl. No.: 14/008,782

(22) PCT Filed: Feb. 7, 2012

(86) PCT No.: PCT/JP2012/052755
§ 371 (c)(1),
(2), (4) Date: Sep. 30, 2013

(87) PCT Pub. No.: WO2012/132557
PCT Pub. Date: Oct. 4, 2012

(65) Prior Publication Data
US 2014/0031778 A1    Jan. 30, 2014

(30) Foreign Application Priority Data

Mar. 29, 2011   (JP) .................................. 2011-072331

(51) Int. Cl.
*A61F 13/15* (2006.01)
*A61L 15/28* (2006.01)
(Continued)

(52) U.S. Cl.
CPC ................. *A61L 15/28* (2013.01); *A61F 13/47* (2013.01); *A61F 13/53* (2013.01); *A61F 13/534* (2013.01); *A61F 2013/530343* (2013.01); *A61F 2013/53445* (2013.01); *A61F 2013/530481* (2013.01)

(58) Field of Classification Search
CPC ... A61F 13/53713; A61F 13/47; A61F 13/53; A61F 13/534; A61F 2013/530343; A61F 2013/530481; A61F 2013/53445; A61F 2013/530372; A61F 2013/530364
See application file for complete search history.

(56) References Cited

U.S. PATENT DOCUMENTS 4,468,428 A    8/1984  Early et al.
5,466,232 A   11/1995  Cadieux et al.
(Continued)

FOREIGN PATENT DOCUMENTS

EP    1013290 A1    6/2000
JP    55-133249 A   10/1980
(Continued)

OTHER PUBLICATIONS

Irwin M. Hunter, Apr. 6, 2007, ElSevier, First edition, pp. 137-138.*
(Continued)

*Primary Examiner* — Bradley Philips
(74) *Attorney, Agent, or Firm* — Hauptman Ham, LLP

(57) ABSTRACT

There is provided an absorbent article with excellent absorption performance. The absorbent article 1 of the invention comprises two or more absorbers 4, 5 that absorb body fluids of a user and are stacked in the thickness direction, a liquid-permeable sheet 2 covering one side of the two or more absorbers, through which body fluid of a user permeates, and a liquid-impermeable sheet 3 covering the other side of the two or more absorbers, through which body fluid of the user does not permeate, wherein the absorber 5 on the liquid-impermeable sheet 3 side of the two or more absorbers 4, 5 contains non-wood pulp and SAP, and the settling velocity of the non-wood pulp in water is between 2 seconds and 5 seconds.

3 Claims, 5 Drawing Sheets

(51) Int. Cl.
*A61F 13/53* (2006.01)
*A61F 13/534* (2006.01)
*A61F 13/47* (2006.01)

(56) References Cited

U.S. PATENT DOCUMENTS

2006/0020250 A1* 1/2006 Chester et al. ................ 604/378
2006/0204723 A1* 9/2006 Bentley et al. ................ 428/171

FOREIGN PATENT DOCUMENTS

JP          60-198151 A      10/1985
JP           2-168949 A       6/1990
JP         2011-015886 A      1/2011

OTHER PUBLICATIONS http://www.naturalfibres2009.org/en/fibres/abaca.html, Oct. 20, 2015.*
http://cdn.intechopen.com/pdfs-wm/44744.pdf, Oct. 20, 2015.*
Extended European Search Report issued Sep. 15, 2014, corresponding European patent application No. 12765088.5.
Corresponding International Application No. PCT/2012/052755 Search Report dated Mar. 13, 2012.

* cited by examiner (a)

(b)

(a)

(b)

(c)

ABSORBENT ARTICLE

RELATED APPLICATIONS

The present application is based on and claims priority to International Application Number PCT/JP2012/052755, filed Feb. 7, 2012, and Japanese Application Number 2011-072331, filed Mar. 29, 2011, the disclosure of which is hereby incorporated by reference herein in its entirety.

TECHNICAL FIELD

The invention relates to an absorbent article containing non-wood pulp.

BACKGROUND ART

Pulp derived from non-wood materials (non-wood pulp) has been used in the past as material for disposable absorbers to be used in diapers and sanitary articles. Bagasse, which consists of the hulls obtained after squeezing juice from sugarcane stems, has been particularly noted as a material for absorbers (PTL 1, for example). By blending pith-containing bagasse pulp and wood pulp, which differ from each other in bulk density, in a prescribed ratio, and thereby adjusting the bulk density, the water retention of the absorber is increased during pressing and compaction.

CITATION LIST

Patent Literature

[PTL 1] Japanese Unexamined Patent Publication No. S55-133249

DISCLOSURE OF THE INVENTION

Technical Problem

However, absorbers containing non-wood pulp have been desired, that have even more excellent rewetting properties and absorption performance than the absorber described in PTL 1 that contains bagasse pulp. It is an object of the present invention to provide an absorbent article comprising an absorber containing non-wood pulp and having excellent absorption performance.

Solution to Problem

In order to solve the aforementioned problem, the invention has the following feature(s).

Specifically, the absorbent article of the invention comprises two or more absorbers that absorb body fluids of a user and are stacked in the thickness direction, a liquid-permeable sheet covering one side of the two or more absorbers, through which body fluid of a user permeates, and a liquid-impermeable sheet covering the other side of the two or more absorbers, through which body fluid of the user does not permeate, wherein the absorber on the liquid-impermeable sheet side of the two or more absorbers contains non-wood pulp and SAP, and the settling velocity of the non-wood pulp in water is between 2 seconds and 5 seconds.

Effect of the Invention

According to the invention, it is possible to obtain an absorbent article with excellent absorption performance.

DESCRIPTION OF EMBODIMENTS

Figure 1:
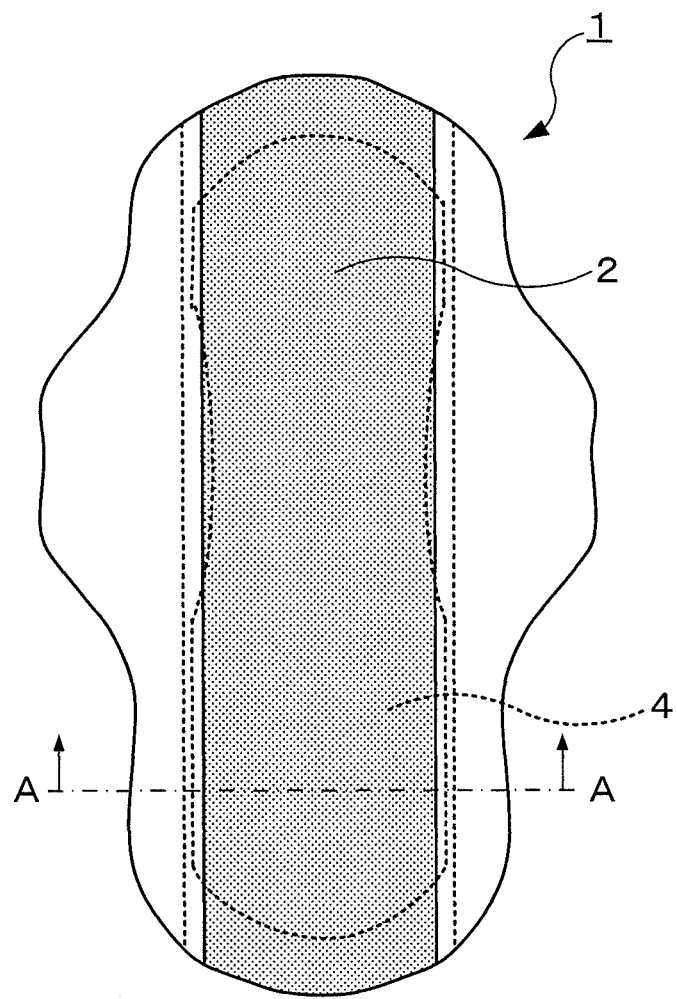
FIG. 1 is a plan view of an absorbent article according to an embodiment of the invention.
Figure 2:
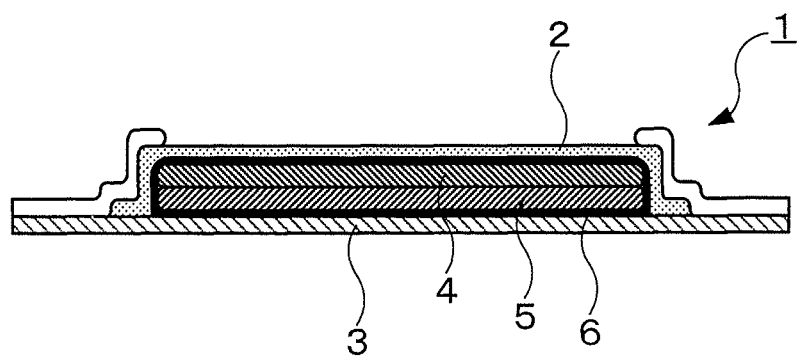
FIG. 2 is a cross-sectional view of the absorbent article of FIG. 1 along A-A.

A sanitary napkin will now be used as an example of an absorbent article according to an embodiment of the absorbent article of the invention, for explanation. FIG. 1 is a plan view of an absorbent article 1 according to an embodiment of the invention, and FIG. 2 is a cross-sectional view of the absorbent article 1 of FIG. 1 along A-A. As shown in FIG. 1 and FIG. 2, the absorbent article 1 has a liquid-permeable front sheet 2, a liquid-impermeable leakproof sheet 3, two absorbers 4, 5 situated between the front sheet 2 and the leakproof sheet 3, and a tissue 6 covering the two absorbers 4, 5. The two absorbers 4, 5 are layered in the thickness direction of the absorbent article. The absorbent article 1 may also comprise three or more absorbers layered in the thickness direction. A second sheet may also be situated between the front sheet 2 and the absorber 4. In this case, a nonwoven fabric with higher density than the front sheet 2 is preferably used as the second sheet, to aid absorption of body fluid from the front sheet 2.

The front sheet 2 is a liquid-permeable sheet that is permeable to body fluids, and it is provided on the front side that contacts with skin of the user, in order to improve the feel on the skin when the user wears the absorbent article 1. Thus, the front sheet 2 preferably has a function of producing a satisfactory feel on the skin. For example, the front sheet 2 may be formed by thin fibers, with a smooth front side and a high degree of freedom against deformation.

A nonwoven fabric is usually used as the front sheet 2. It may be formed by an air-through method using a known carded web. A method for producing a nonwoven fabric to be used for the front sheet 2 is not limited to the aforementioned air-through method, and for example, a nonwoven fabric may be produced by a needle punching or spunlace method wherein a fiber web is entangled to form a stable sheet, a binder bonding or thermal bonding method wherein a web is anchored by bonding the fibers or melting the fibers themselves, a spunbond method wherein sealing is accomplished using filament fibers, or a wet method involving sheet formation by paper-making.

The fibers to be used in the nonwoven fabric of the front sheet 2 are composed of, for example, linear low-density polyethylene (LLDPE), low-density polyethylene (LDPE), medium-density polyethylene (MDPE), high-density polyethylene (HDPE), polypropylene, polybutylene and copolymers composed mainly thereof, ethylene-vinyl acetate copolymer (EVA), ethylene-ethyl acrylate copolymer (EEA), ethylene-acrylic acid copolymer (EAA), polyolefin-based resins such as ionomer resins, polyester-based resins such as polyethylene terephthalate (PET), polybutylene terephthalate (PBT), polytrimethylene terephthalate (PTT) and polylactic acid, and polyamide-based resins such as nylon, as well as mixtures of the foregoing.

The leakproof sheet 3 is a liquid-impermeable sheet that is not permeable to body fluids, and it is provided so that discharged body fluids do not leak to the outside. The material of the leakproof sheet 3 is not particularly restricted so long as it is a material through which discharged body fluids do not permeate. For example, a waterproof treated nonwoven fabric, a plastic film made of polyethylene or the like, or a composite material of a nonwoven fabric and a plastic film, may be used as the leakproof sheet 3.

The two absorbers 4, 5 have the function of absorbing and retaining discharged body fluid. The two absorbers 4, 5 are layered in the thickness direction of the absorbent article 1. The absorbing material used for the absorber 4 situated on the front sheet 2 side of the two absorbers 4, 5 is preferably wood pulp or pulp obtained from a non-wood material (hereunder referred to as "non-wood pulp"). The absorbing material used for the absorber 5 situated on the leakproof sheet 3 side is preferably a mixture of non-wood pulp and a super-absorbent polymer (SAP). When the absorbing material used for the absorber 4 situated on the front sheet 2 side is wood pulp, the mean fiber size of the wood pulp is preferably larger than the mean fiber size of the non-wood pulp used in the absorber 5 situated on the leakproof sheet 3 side.

Wood pulp is pulp obtained from a wood material, such as needle bleached softwood kraft pulp (NBKP) or leaf bleached hardwood kraft pulp (LBKP). Non-wood pulp is pulp other than wood pulp obtained from a plant material, and non-wood pulp includes, for example, linter pulp, Manila hemp, kenaf, esparto grass, straw, bamboo or banana stem. The non-wood pulp to be used for the absorber 5 is preferably abaca pulp made from Manila hemp, and in particular a portion near the core of Manila hemp or a portion between the core and hull of Manila hemp, or banana pulp made from banana stem.

Figure 7:
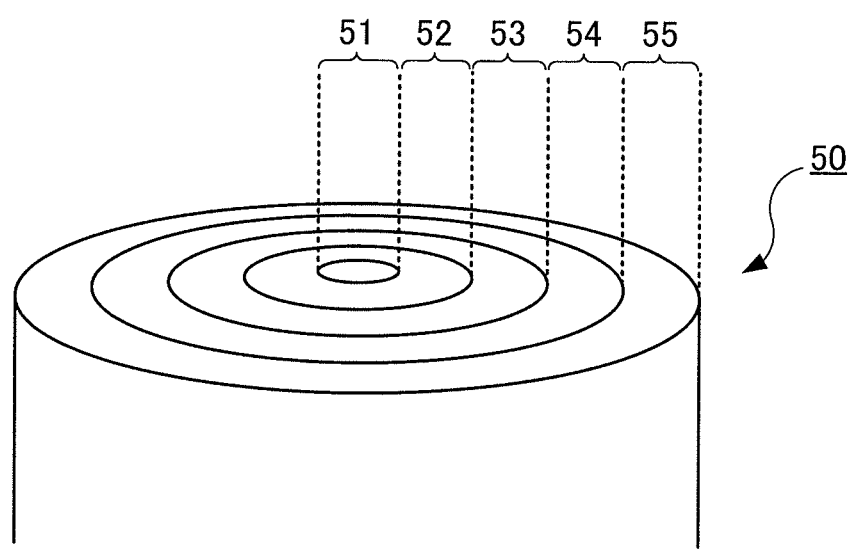
FIG. 7 is a diagram for illustration of the cross-sectional structure of Manila hemp.

The portion near the core of Manila hemp and the portion between the core and the hull of Manila hemp will now be explained with reference to FIG. 7. As shown in FIG. 7, the cross-sectional structure of the Manila hemp 50 is classified as the core 51, the portion near the core 52, the intermediate portion 53, the portion adjacent to the outside 54 and the outside 55, of Manila hemp 50. The phrase "portion near the core of Manila hemp" as used herein corresponds to the portion near the core 52 and the intermediate portion 53 of Manila hemp 50, and the "portion between the core and hull of Manila hemp" corresponds to the portion adjacent to the outside 54 of Manila hemp 50.

Abaca fiber formed from Manila hemp is classified by the portion of the Manila hemp starting material. Specifically, abaca fiber is classified as whether the starting material portion is the core 51, the portion near the core 52, the intermediate portion 53, the portion adjacent to the outside 54 or the outside 55 of Manila hemp 50. For example, abaca fiber is classified as special grade AD, EF, S2 or S3, depending on the portion that is the Manila hemp starting material. AD represents abaca fiber made from the portion near the core 52 of Manila hemp 50. AD abaca fiber is pure white fiber with gloss. EF represents abaca fiber made from the intermediate portion 53 of Manila hemp 50. EF abaca fiber is fiber from the soft pure fiber center portion, and is light ivory-colored. S2 represents abaca fiber made from the portion adjacent to the outside 54 of Manila hemp 50. S2 abaca fiber is light-yellow or light-violet colored. S3 represents abaca fiber made from the outside 55 of Manila hemp 50. S3 abaca fiber is dark-red or violet-colored, and is mainly used in rope.

Abaca fiber can also be classified as special grade I, G or H, depending on the portion of the Manila hemp starting material. I represents abaca fiber made from the intermediate portion 53 of Manila hemp 50. I abaca fiber is pale yellow-colored. G represents abaca fiber made from the intermediate portion 53 of Manila hemp 50. G represents abaca fiber made from the portion adjacent to the outside 54 of Manila hemp 50. G abaca fiber is dull, dark white-colored, and tends to form bundles. H represents abaca fiber made from the outside 55 of Manila hemp 50. H abaca fiber is nearly black, dark brown-colored, and is mainly used in rope.

Abaca fiber can also be classified as special grade JK or M1, depending on the portion of the Manila hemp starting material. JK represents abaca fiber made from the portion adjacent to the outside 54 of Manila hemp 50. JK abaca fiber is tan or light-green colored, and is used mainly as pulp. M1 represents abaca fiber made from the outside 55 of Manila hemp 50. M1 abaca fiber is dark brown to black fiber, and is mainly used in rope.

Abaca fiber from the "portion near the core of Manila hemp" corresponds to abaca fiber AD, EF or I, and abaca fiber from the "portion between the core and hull of Manila hemp" corresponds to abaca fiber S2, G or JK. Abaca fiber from the hull corresponds to abaca fiber S3, H or M1.

When the absorbent article 1 comprises three or more absorbers layered in the thickness direction, at least the absorbing material used for the absorber situated on the outermost front sheet side is preferably wood pulp or pulp from a non-wood material (hereunder referred to as "non-wood pulp"), and the absorbing material used for the absorber on the outermost leakproof sheet side is preferably a mixture of non-wood pulp and SAP.

The mean fiber size of the non-wood pulp to be used in the absorber 5 on the leakproof sheet 3 side is preferably 8 μm to 25 μm and more preferably 10 μm to 20 μm. This increases the number of fibers per unit volume in the absorber 5, allowing the absorber 5 to be easily increased in thickness and the apparent bulk density to be lowered. Thus, the volume required to store absorbed user body fluids will be more easily ensured in the absorber 5. Also, since the specific surface area and the void volume between fibers of the non-wood pulp are increased, it is possible to increase the amount of absorption by the absorber 5. Furthermore, since the distance between fibers of the non-wood pulp is reduced, the force of drawing body fluids by capillary movement of the non-wood pulp is increased. In addition, tangling occurs more readily between the fibers of the non-wood pulp and between the non-wood pulp fibers and SAP, so that the absorber does not disintegrate and the shape of the absorber can be maintained, even with reduced weight and thinning of the absorber. If the mean fiber size of the non-wood pulp is smaller than 8 μm, it will be difficult to maintain the hollow structure, and bulk maintenance can potentially become impaired. If the mean fiber size of the non-wood pulp is larger than 25 μm, the effect described above may be lessened. Non-wood pulp fibers tend to intervene between SAP particles, thus allowing gel blocking to be inhibited.

The lignin content of the non-wood pulp used in the absorber 5 is preferably not greater than 0.5 mass % and more preferably not greater than 0.3 mass %. If the lignin content of the non-wood pulp used in the absorber 5 is greater than 0.5 mass %, the mean fiber size of the non-wood pulp used in the absorber 5 will be increased, the apparent bulk density of the absorber 5 will be increased, and the hydrophilicity of the non-wood pulp will be lowered, thereby potentially reducing the water absorption performance of the absorber 5.

The settling velocity of the non-wood pulp used in the absorber 5 is preferably between 2 seconds and 5 seconds, and more preferably between 2.5 seconds and 4 seconds. In this case, it is expected that the structure of the non-wood pulp fibers is a hollow structure, and that the non-wood pulp fibers are hydrophilic, and therefore the absorption of user body fluids by the absorber 5 increases. The settling velocity is the time from contact of a basket containing the non-wood pulp with a water surface, until settling occurs under the water surface, as measured in the following manner.

A 5.0 g portion of non-wood pulp is evenly packed into a cylindrical basket. The basket is formed of copper wire, the diameter of the copper wire being 0.4 mm. The weight of the basket was 3 g, the diameter was 50 mm and the height was 80 mm. The spacing between copper wires of the basket mesh is 20 mm. Ion-exchanged water is added until the water depth reaches 200 mm in a 2 liter beaker. The basket containing the non-wood pulp is then dropped from a height of 10 mm from the water surface, and the time from contact of the basket with the water surface until progression under the water surface is measured. The measured time is the settling velocity of the non-wood pulp.

If the structure of the non-wood pulp fibers is a hollow structure, the hollow structure will contain air, and settling of the non-wood pulp will thus be delayed. If the settling velocity of the non-wood pulp is less than 2 seconds, the porosity of the non-wood pulp fibers is low and they may not be hollow, and thus absorption of body fluids by the absorber 5 may be reduced. If the settling velocity of the non-wood pulp is greater than 5 seconds, the non-wood pulp fibers may have low hydrophilicity, and absorption of body fluids by the absorber 5 may be reduced.

The apparent bulk density of the non-wood pulp used in the absorber 5 is preferably between 0.04 g/cm$^3$ and 0.07 g/cm$^3$. This will increase the volume in the absorber 5 for storing absorbed user body fluids, and will increase absorption by the absorber 5. If the apparent bulk density of the non-wood pulp is lower than 0.04 g/cm$^3$, the absorber strength may be reduced and the shape retention may be impaired. If the apparent bulk density of the non-wood pulp is higher than 0.07 g/cm$^3$, the volume for storing absorbed user body fluids may be reduced, and absorption by the absorber 5 may be lowered.

The absorption of the non-wood pulp used in the absorber 5 for 0.9% physiological saline is preferably at least 20 times the mass of the non-wood pulp. Thus, it is possible to obtain an absorber with equivalent absorption while using a smaller amount of non-wood pulp than wood pulp, and to decrease the weight and reduce the thickness of the absorber. If the absorption of the non-wood pulp for 0.9% physiological saline is less than 20-fold, the absorption of the absorber using non-wood pulp will not be significantly different from the absorption of an absorber using wood pulp, and therefore the effect of using the non-wood pulp instead of wood pulp for absorption by the absorber 5 may be reduced.

The non-wood pulp used in the absorber 4 on the front sheet 2 side is preferably non-wood pulp suited for the absorber 5 on the leakproof sheet 3 side. The non-wood pulp used in the absorber 4 on the front sheet 2 side may be the same as or different from the non-wood pulp used in the absorber 5 on the leakproof sheet 3 side.

Body fluid discharged by the user is rapidly absorbed into the absorber 4 on the front sheet 2 side, and migrates into the absorber 5 on the leakproof sheet 3 side. The absorber 5 on the leakproof sheet 3 side contains non-wood pulp that has rapid absorption and allows absorbed body fluid to rapidly migrate into the SAP, and SAP that has excellent water retention, and therefore body fluid discharged by the user is rapidly absorbed into the SAP. Since body fluid that has been absorbed into SAP is not easily discharged from the SAP by applying pressure to the SAP, the body fluid absorbed into the absorber 5 does not easily return to the front sheet 2, even when user body pressure is exerted on the absorbent article 1. In addition, body fluid that has been discharged from the absorber 5 by body pressure of the user onto the absorbent article 1 must pass through the absorber 4 on the front sheet 2 side in order to return to the front sheet 2. Therefore, body fluid that has been discharged from the absorber 5 by body pressure of the user onto the absorbent article 1 is absorbed into the absorber 4 on the front sheet 2 side. Consequently, the rewetting amount of the absorbent article 1 is reduced by layering the two absorbers 4, 5 in the thickness direction and placing them on the absorbent article 1.

A tissue 6 covers the two absorbers 4, 5 together, to prevent disintegration and loss of integrity of the absorbers 4, 5. When the absorbers 4, 5 do not disintegrate even in the absence of the tissue 6, the absorbent article 1 does not need to have the tissue 6.

The absorbent article of the invention also encompasses absorbent articles that are to be used by animals other than humans, such as pets, in addition to absorbent articles used by humans. Animals that use the absorbent article, including humans and animals other than humans such as pets, will be referred to as "users".

EXAMPLES

The present invention will now be explained in greater detail by examples, with the understanding that these examples are in no way limitative on the invention.

In the examples, comparative examples and reference examples, the absorption rates and rewetting amounts were measured in the following manner.

(1) A cylinder with an inner diameter of 60φ and a height of 50 mm was installed on the front sheet of the absorbent article sample, at the section corresponding to the center section of the absorber.

(2) The cylinder was injected with 80 mL of 0.9% physiological saline for 10 seconds. The 0.9% physiological saline was the same as the 0.9% physiological saline mentioned below.

(3) The time was measured from initial injection of the 0.9% physiological saline until the 0.9% physiological saline was absorbed into the absorbent article sample and disappeared from the cylinder. The measured time was recorded as the absorption rate (sec).

(4) The cylinder was removed from the absorbent article sample after 5 minutes from initial injection of the 0.9% physiological saline, approximately 50 g of filter paper (100 mm×100 mm) whose mass had been measured beforehand was placed on the absorbent article sample, and a 3.5 kg weight (100 mm×100 mm) was placed on the filter paper.

(5) At 3 minutes after placement of the weight, the filter paper was removed and the mass of the filter paper was measured. Also, the mass of the filter paper before placement on the absorbent article sample was subtracted from the mass of the filter paper after placement, to determine the rewetting amount of the absorbent article sample.

(6) The process from injection of the 0.9% physiological saline until calculation of the rewetting amount of the absorbent article sample was carried out three times every 10 minutes, and data for the absorption rate and rewetting amount were recorded three times.

Also, the mean fiber sizes, lignin contents, settling velocities, fiber specific gravities, apparent bulk densities, absorptions, pressed water capacities and water capacities of the ground pulps used in the examples, comparative examples and reference examples were measured in the following manner.

(Mean Fiber Size)

A Fiber Lab 3.8 Kajaani fiber length analyzer by Metso Automation Co. was used to measure approximately 20,000 fibers, and the mean fiber size was recorded.

(Lignin Content)

The lignin content of the pulp was measured according to the method of P. J. Van Soest et al. (Proc. Nutr. Soc., 32123 (1973)).

(Settling Velocity)

(1) A 5.0 g portion of non-wood pulp was evenly packed into a cylindrical basket. The basket was formed of copper wire, the diameter of the copper wire being 0.4 mm. The weight of the basket was 3 g, the diameter was 50 mm and the height was 80 mm. The spacing between copper wires of the basket mesh was 20 mm.

(2) Ion-exchanged water was added until the water depth reached 200 mm in a 2 liter beaker.

(3) The basket containing the non-wood pulp was dropped from a height of 10 mm from the surface of water in a 2 liter beaker, and the time from contact of the basket with the water surface until progression under the water surface was measured. The measured time was recorded as the settling velocity of the non-wood pulp.

(Fiber Specific Gravity)

The fiber specific gravity of the pulp was measured according to JIS M 8717, using a He gas comparative densitometer (manufactured by of Tokyo Science Co., Ltd.).

(Apparent Bulk Density)

A 10 g portion of ground pulp was layered at 100 mm×100 mm. A 100 mm×100 mm board was placed over the layered ground pulp and a 100 g load weight was placed over it. The thickness of the layered ground pulp at 10 seconds after placement of the weight was used as the apparent bulk, and the apparent bulk density was calculated.

(Absorption, Pressed Water Capacity, Water Capacity)

(1) After placing 1000 mL of 0.9% physiological saline in a 2 L beaker, the liquid temperature was measured. The 0.9% physiological saline was prepared by placing 27.0 g of sodium chloride (extra pure reagent grade) in a 3 L beaker, and then adding ion-exchanged water to the 3 L beaker until the total amount of ion-exchanged water and sodium chloride reached 3000.0 g.

Figure 3:
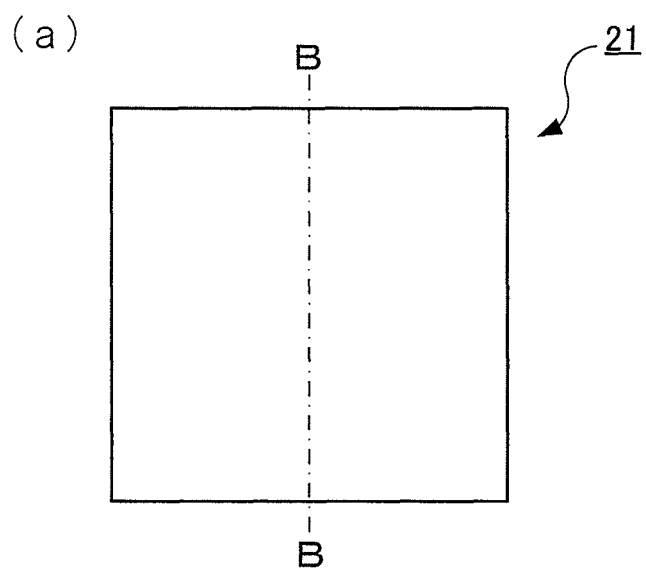
FIG. 3 is a diagram for illustration of a nylon mesh bag to be used for measurement of absorption.
Figure 3:
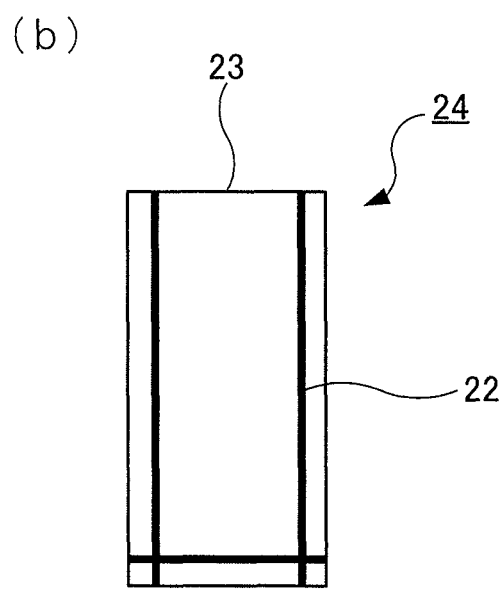

(2) A 250-mesh nylon mesh (N-NO250HD by NBC Industries) was cut to a size of 200 mm×200 mm and the mass (x(g)) was measured, after which it was folded at the section of the dotted line B-B shown in FIG. 3(a) to fold the nylon mesh 21 in half. As shown in FIG. 3(b), it was placed with the folded section at the right, and then heat seals 22 were formed at a location 5 mm above the bottom edge, a location 5 mm to the left of the right edge and a location 5 mm to the right of the left edge, to form a nylon mesh bag 24 with an open top edge 23. The pulverized pulp (y(g)) whose mass had been previously measured was placed in the nylon mesh bag 24, and a heat seal (not shown) was formed to close the open top edge 23 of the nylon mesh bag 24.

(3) The bag containing the ground pulp was dipped into the beaker containing the physiological saline so as to touch the bottom, and allowed to stand for 3 minutes.

(4) After standing, the bag containing the ground pulp was lifted, and allowed to stand naturally for draining, for a period of 3 minutes.

(5) The weight ($z_1$ (g)) of the bag containing the ground pulp was measured.

(6) The absorption factor was calculated by the following formula.

$$\text{Absorption}(g/g) = ((z_1 - x) - y)/y$$

(7) An acrylic board was placed on the bag containing the ground pulp that had been measured in (6), and a 100 mm×100 mm weight with a load of 3.5 kg was further placed on the acrylic board and allowed to stand for 3 minutes.

(8) The weight and acrylic board were removed, and the weight ($z_2$ (g)) of the bag containing the ground pulp was measured.

(9) The pressed water capacity was calculated by the following formula.

$$\text{Pressed water capacity}(g/g) = ((z_2 - x) - y)/y$$

(10) The bag containing the ground pulp that had been measured in (8) was dewatered with a centrifugal separator. The centrifugal separator used was a Model H130 separator by Kokusan Co., Ltd. The rotational speed of the centrifugal separator was 850 rpm (150 G).

(11) The weight ($z_3$ (g)) of the dewatered bag containing the absorbing material was measured.

(12) The water capacity was calculated by the following formula.

$$\text{Water capacity }(g/g) = ((z_3\_x) - y)/y$$

(Ground Pulp 1)

Abaca BKP (AK104 by Ogura Trading Co., Ltd.) as pulp obtained from the portion near the core of Manila hemp, was pulverized into a fibrous state to prepare ground pulp 1.

(Ground Pulp 2)

Abaca BKP (AK102 by Ogura Trading Co., Ltd.) as pulp obtained from the portion between the core and hull of Manila hemp, was pulverized into a fibrous state to prepare ground pulp 2.

(Ground Pulp 3)

Banana BKP (Ogura Trading Co., Ltd.) as pulp obtained from banana stems, was pulverized into a fibrous state to prepare ground pulp 3.

(Ground Pulp 4)

Ground pulp 4 was prepared by pulverizing wood pulp (needle bleached softwood Kraft pulp (NBKP)) into a fibrous form.

(Ground Pulp 5)

Ground pulp 5 was prepared by pulverizing bagasse BKP (Ogura Trading Co., Ltd.) into a fibrous state.

(Ground Pulp 6)

Ground pulp 6 was prepared by pulverizing kenaf BKP (Ogura Trading Co., Ltd.) into a fibrous state.

Example 1

Figure 4:
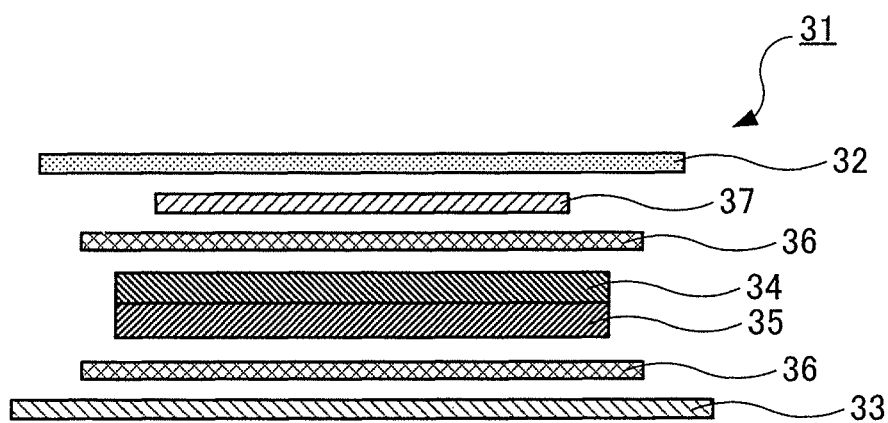
FIG. 4 is a diagram for illustration of the construction of an absorbent article sample.

Ground pulp 4 having a basis weight of 100 g/m$^2$ was used to produce an absorber for a front sheet side. Ground pulp 1 having a basis weight of 150 g/m$^2$ was uniformly blended with SAP having a basis weight of 250 g/m$^2$ (AQUA KEEP SA60S, product of Sumitomo Seika Chemicals Co., Ltd.) to produce an absorber for a leakproof sheet side. In Example 1, an absorbent article sample was produced as an absorbent article sample 31 having the structure shown in FIG. 4, comprising a front sheet 32, a second sheet 37, a tissue 36, an absorber 34 on the front sheet 32 side, an absorber 35 on the leakproof sheet 33 side and a leakproof sheet 33. The front sheet 32 was an air-through nonwoven fabric with a basis weight of 25 g/m$^2$, the second sheet 37 was an air-through nonwoven fabric with a basis weight of 20 g/m², the basis weight of the tissue 36 was 17 g/m² and the basis weight of the leakproof sheet 33 was 17 g/m². Each member was attached using a spiral hot-melt adhesive. The coating weight of the spiral hot-melt adhesive was 5 g/m².

Example 2

Ground pulp 4 having a basis weight of 150 g/m² was used to produce an absorber for a front sheet side. Ground pulp 1 having a basis weight of 100 g/m² was uniformly blended with SAP having a basis weight of 250 g/m² (AQUA KEEP SA60S, product of Sumitomo Seika Chemicals Co., Ltd.) to produce an absorber for a leakproof sheet side. These absorbers were used to produce an absorbent article sample of Example 2, as an absorbent article sample 31 having the structure shown in FIG. 4.

Example 3

Ground pulp 1 having a basis weight of 100 g/m² was used to produce an absorber for a front sheet side. Ground pulp 1 having a basis weight of 150 g/m² was uniformly blended with SAP having a basis weight of 250 g/m² (AQUA KEEP SA60S, product of Sumitomo Seika Chemicals Co., Ltd.) to produce an absorber for a leakproof sheet side. These absorbers were used to produce an absorbent article sample of Example 3, as an absorbent article sample 31 having the structure shown in FIG. 4.

Reference Example 1

Figure 5:
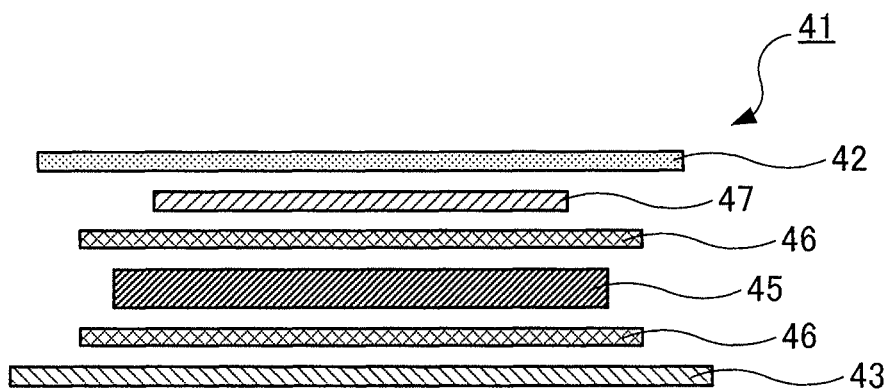
FIG. 5 is a diagram for illustration of a different construction of an absorbent article sample.

An absorber was prepared comprising a uniform mixture of ground pulp 1 having a basis weight of 250 g/m² and SAP having a basis weight of 250 g/m² (AQUA KEEP SA60S by Sumitomo Seika Chemicals Co., Ltd.), to produce an absorbent article sample of Reference Example 1 as an absorbent article sample 41 having the structure shown in FIG. 5, comprising a front sheet 42, a second sheet 47, a tissue 46, an absorber 45 and a leakproof sheet 43. The front sheet 42 was an air-through nonwoven fabric with a basis weight of 25 g/m², the second sheet 47 was an air-through nonwoven fabric with a basis weight of 20 g/m², the basis weight of the tissue 46 was 17 g/m² and the basis weight of the leakproof sheet 43 was 17 g/m². Each member was attached using a spiral hot-melt adhesive.

The coating weight of the spiral hot-melt adhesive was 5 g/m².

Reference Example 2

An absorber was prepared comprising a uniform mixture of ground pulp 2 having a basis weight of 250 g/m² and SAP having a basis weight of 250 g/m² (AQUA KEEP SA60S by Sumitomo Seika Chemicals Co., Ltd.), to produce an absorbent article sample of Reference Example 2 as an absorbent article sample 41 having the structure shown in FIG. 5.

Reference Example 3

An absorber was prepared comprising a uniform mixture of ground pulp 3 having a basis weight of 250 g/m² and SAP having a basis weight of 250 g/m² (AQUA KEEP SA60S by Sumitomo Seika Chemicals Co., Ltd.), to produce an absorbent article sample of Reference Example 3 as an absorbent article sample 41 having the structure shown in FIG. 5.

Reference Example 4

An absorber was prepared comprising a uniform mixture of ground pulp 5 having a basis weight of 250 g/m² and SAP having a basis weight of 250 g/m² (AQUA KEEP SA60S by Sumitomo Seika Chemicals Co., Ltd.), to produce an absorbent article sample of Reference Example 4 as an absorbent article sample 41 having the structure shown in FIG. 5.

Reference Example 5

An absorber was prepared comprising a uniform mixture of ground pulp 6 having a basis weight of 250 g/m² and SAP having a basis weight of 250 g/m² (AQUA KEEP SA60S by Sumitomo Seika Chemicals Co., Ltd.), to produce an absorbent article sample of Reference Example 5 as an absorbent article sample 41 having the structure shown in FIG. 5.

Comparative Example 1

An absorber was prepared comprising a uniform mixture of ground pulp 4 having a basis weight of 250 g/m² and SAP having a basis weight of 250 g/m² (AQUA KEEP SA60S by Sumitomo Seika Chemicals Co., Ltd.), to produce an absorbent article sample of Comparative Example 1 as an absorbent article sample 41 having the structure shown in FIG. 5.

Comparative Example 2

Ground pulp 4 having a basis weight of 100 g/m² was used to produce an absorber for a front sheet side. Ground pulp 4 having a basis weight of 150 g/m² was uniformly blended with SAP having a basis weight of 250 g/m² (AQUA KEEP SA60S, product of Sumitomo Seika Chemicals Co., Ltd.) to produce an absorber for a leakproof sheet side. These absorbers were used to produce an absorbent article sample of Comparative Example 2, as an absorbent article sample 31 having the structure shown in FIG. 4.

Comparative Example 3

Ground pulp 1 having a basis weight of 100 g/m² was used to produce an absorber for a front sheet side. Ground pulp 4 having a basis weight of 150 g/m² was uniformly blended with SAP having a basis weight of 250 g/m² (AQUA KEEP SA60S, product of Sumitomo Seika Chemicals Co., Ltd.) to produce an absorber for a leakproof sheet side. These absorbers were used to produce an absorbent article sample of Comparative Example 2, as an absorbent article sample 31 having the structure shown in FIG. 4.

In order to allow comparison of the performances of the absorbers of Examples 1 to 3, Comparative Examples 1 to 3 and Reference Examples 1 to 5, absorbent article samples 31 and 41 were produced with total absorber weights of about 29.5 g.

The results for the mean fiber size, lignin content, settling velocity, fiber specific gravity, apparent bulk density, absorption, pressed water capacity and water capacity for each of the ground pulps 1 to 6 are shown in Table 1 below.

TABLE 1

Mean fiber size, lignin content, settling velocity, fiber specific gravity, apparent bulk density, absorption, pressed water capacity and water capacity for examples and comparative examples

| | Type of starting material | Type of pulp | Mean fiber size (μm) | Lignin content (wt %) | Settling velocity (sec) | Fiber specific gravity (g/cm³) | Apparent bulk density (g/cm³) | Absorption (g/g) | Pressed water capacity (g/g) | Water capacity (g/g) |
|---|---|---|---|---|---|---|---|---|---|---|
| Ground pulp 1 | Manila hemp (near core) | ABACA BKP (AK104) | 17.9 | <0.2 | 3.30 | 1.52 | 0.054 | 25.7 | 19.0 | 7.8 |
| Ground pulp 2 | Manila hemp (portion between core and hull) | ABACA BKP (AK102) | 18.0 | <0.2 | 3.32 | 1.57 | 0.065 | 22.5 | 18.8 | 7.8 |
| Ground pulp 3 | Banana (stem) | Banana BKP | 12.5 | 0.3 | 2.84 | 1.46 | 0.048 | 25.9 | 13.9 | 8.2 |
| Ground pulp 4 | Softwood (Douglas fir) | Wood pulp (NBKP) | 34.5 | <0.2 | 1.04 | 1.45 | 0.083 | 16.2 | 12.0 | 8.4 |
| Ground pulp 5 | Sugar cane (bagasse) | Bagasse BKP | 12.6 | <0.2 | 1.26 | 1.50 | 0.061 | 18.8 | 16.0 | 8.3 |
| Ground pulp 6 | Kenaf (Bast) | Kenaf BKP | 12.6 | <0.2 | 1.82 | 1.50 | 0.059 | 19.2 | 12.3 | 8.4 |

The results for the properties as well as the absorber thickness, absorption rate and rewetting amount in Examples 1 to 3, Comparative Examples 1 to 3 and Reference Examples 1 to 5, are shown in Table 2 below.

TABLE 2

Properties and absorption thickness, absorption speed and rewetting amounts for absorbent article samples of examples and comparative examples

| | Upper layer ground pulp | Lower layer ground pulp | Upper layer pulp basis weight (g/m²) | Lower layer pulp basis weight (g/m²) | Lower layer SAP basis weight (g/m²) | Absorber mass (g) | Absorption speed 1st time (sec) | Absorption speed 2nd time (sec) | Absorption speed 3rd time (sec) | Rewetting amount 1st time (g) | Rewetting amount 2nd time (g) | Rewetting amount 3rd time (g) |
|---|---|---|---|---|---|---|---|---|---|---|---|---|
| Example 1 | Ground pulp 4 | Ground pulp 1 | 100 | 150 | 250 | 29.7 | 10.4 | 10.8 | 11.8 | 0.18 | 3.11 | 12.48 |
| Example 2 | Ground pulp 4 | Ground pulp 1 | 150 | 100 | 250 | 29.6 | 11.5 | 12.3 | 14.3 | 0.19 | 3.00 | 13.84 |
| Example 3 | Ground pulp 1 | Ground pulp 1 | 100 | 150 | 250 | 29.6 | 10.4 | 10.8 | 12.2 | 0.21 | 3.02 | 14.53 |
| Reference Example 1 | — | Ground pulp 1 | — | 250 | 250 | 29.4 | 11.0 | 10.6 | 12.7 | 0.21 | 5.84 | 15.22 |
| Reference Example 2 | — | Ground pulp 2 | — | 250 | 250 | 29.5 | 11.5 | 12.1 | 17.3 | 0.20 | 7.14 | 16.31 |
| Reference Example 3 | — | Ground pulp 3 | — | 250 | 250 | 29.3 | 10.2 | 10.8 | 11.6 | 0.15 | 4.35 | 14.40 |
| Reference Example 4 | — | Ground pulp 5 | — | 250 | 250 | 29.5 | 11.4 | 14.3 | 22.4 | 0.22 | 7.78 | 13.01 |
| Reference Example 5 | — | Ground pulp 6 | — | 250 | 250 | 29.4 | 11.0 | 13.8 | 23.1 | 0.24 | 8.01 | 18.15 |
| Comparative Example 1 | — | Ground pulp 4 | — | 250 | 250 | 29.6 | 11.3 | 14.1 | 26.8 | 0.26 | 8.54 | 18.61 |
| Comparative Example 2 | Ground pulp 4 | Ground pulp 4 | 100 | 150 | 250 | 29.5 | 11.7 | 13.6 | 17.4 | 0.23 | 3.75 | 30.62 |
| Comparative Example 3 | Ground pulp 1 | Ground pulp 4 | 100 | 150 | 250 | 29.7 | 11.4 | 13.8 | 19.5 | 0.25 | 9.48 | 33.41 |

Ground pulps 1 to 3 all had absorption for 0.9% physiological saline that was at least 20 times the mass of the pulp. Also, ground pulps 1 to 3 all had settling velocities between 2 seconds and 5 seconds. In addition, ground pulps 1 to 3 all had mean fiber sizes of 8 μm to 25 μm, lignin contents of not greater than 0.5 mass %, and apparent bulk densities of 0.04 g/cm³ to 0.07 g/cm³.

Ground pulp 4 had a large mean fiber size of 34.5 μm, a rapid settling velocity of 1.04 seconds, a large apparent specific gravity of 0.083 g/cm³, and a low absorption of 0.9% physiological saline, of 16.2 times the pulp mass. Ground pulp 5 had a rapid settling velocity of 1.26 seconds, and a low absorption of 0.9% physiological saline, of 18.8 times the pulp mass. Ground pulp 6 had a rapid settling velocity of 1.82 seconds, and a low absorption of 0.9% physiological saline, of 19.2 times the pulp mass.

Figure 6:
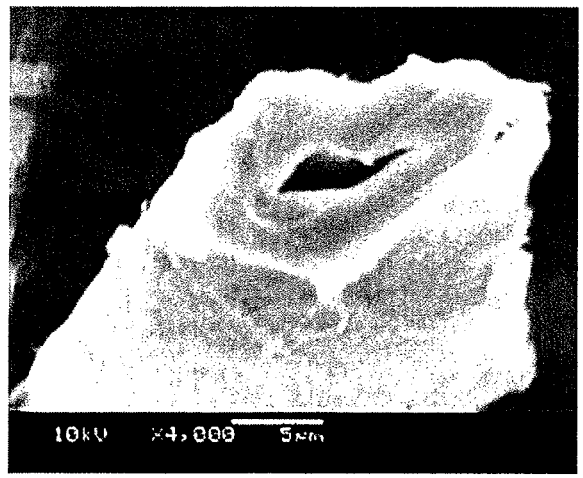
FIG. 6 is a scanning electron micrograph of a cross-section of a ground pulp fiber.
Figure 6:
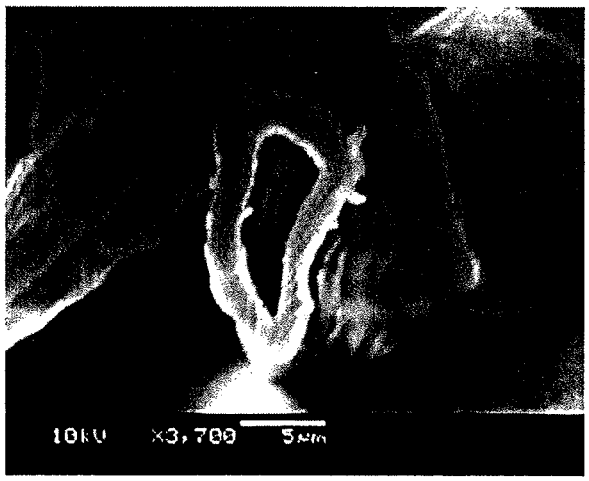
Figure 6:
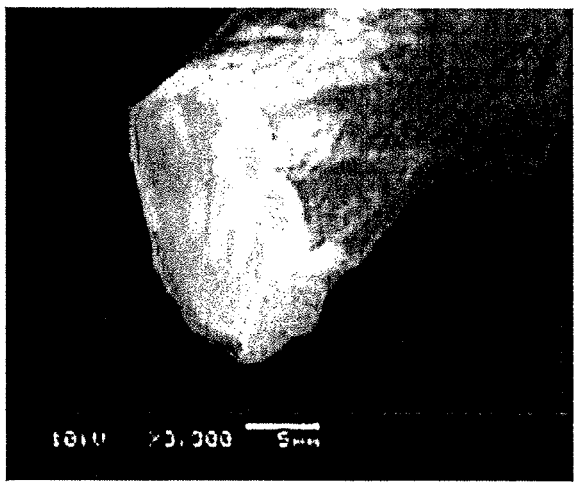

Ground pulps 1 and 2, which were abaca pulp, had absorptions of at least 50% higher than ground pulp 4 which was wood pulp, and therefore body fluids can be absorbed in levels equivalent to wood pulp with smaller amounts than wood pulp. Also, since the water capacities of ground pulps 1 and 2 were equal to or less than that of the wood pulp of ground pulp 4, transfer of liquid from the pulp fibers of ground pulps 1 and 2 into the SAP was satisfactory, and the repeated absorption performance was also satisfactory. The property of Examples 1 and 2, of low water capacity despite large absorption, was also exhibited by ground pulp 3 which was banana pulp. The property of ground pulps 1 to 3 of low water capacity despite large absorption, is thought to be due to the hollow structure of the fibers of ground pulps 1 to 3. FIG. 6 shows scanning electron microscope (SEM) photographs of cross-sections of a fiber of abaca pulp, banana pulp and wood pulp, respectively. FIG. 6(*a*) is a SEM photograph of the cross-section of an abaca pulp fiber, FIG. 6(*b*) is a SEM photograph of the cross-section of a banana pulp fiber, and FIG. 6(*c*) is a SEM photograph of the cross-section of a wood pulp fiber. Abaca pulp is expected to have excellent water uptake into the fiber interiors and excellent pressed water retention, due to voids between the hollow structure fibers. Banana pulp takes up water in the fiber interiors and between the fibers due to the narrowness of the fibers and the voids between fibers, and is therefore expected to have excellent diffusibility, pressed water retention and water retention. The pressed water capacities of ground pulps 1 and 2 were at least 50% higher than that of the wood pulp of ground pulp 4, and therefore the rewetting amount of the absorber is low even if body pressure is applied to the absorber before transfer of liquid from the pulp fiber into the SAP.

Reference Examples 1 to 3 had rapid absorption of 0.9% physiological saline and low rewetting amounts. This indicated that the absorption properties of the absorbent article samples produced using ground pulps 1 to 3 were excellent. That is, it was shown that the absorption properties were excellent with absorbent article samples using ground pulp having absorption for 0.9% physiological saline that was at least 20-fold with respect to the pulp mass. In addition, it was shown that the absorption properties were excellent with absorbent article samples using ground pulp having a settling velocity of between 2 seconds and 5 seconds. Furthermore, it was shown that the absorption properties were excellent with absorbent article samples using ground pulp having a mean fiber size of between 8 µm and 25 µm and an apparent bulk density of between 0.04 g/cm$^3$ and 0.07 g/cm$^3$.

The absorption of 0.9% physiological saline in Reference Examples 4 and 5 and Comparative Example 1 was rapid for the first and second measurements, but slow for the third measurement. That is, the repeated absorption properties of Reference Examples 4 and 5 and Comparative Example 1 were poor. Reference Examples 4 and 5 and Comparative Example 1 had low rewetting amounts for the first measurement, but high rewetting amounts for the second and subsequent measurements.

When Example 3 and Reference Example 1 were compared, it was seen that if a single-layer absorber using non-wood pulp is replaced with a two-layer absorber using non-wood pulp, this reduces the rewetting amount of the absorbent article. When Examples 1 and 2 and Example 3 were compared, it was seen that changing the absorbing material of the absorber on the front sheet side from non-wood pulp to wood pulp increases the rewetting amount of the absorbent article. However, as clearly seen by comparing Examples 1 and 2 with Comparative Examples 1 and 2, Examples 1 and 2 had low rewetting amounts compared to the absorbent articles comprising absorbers using only wood pulp as pulp.

When Comparative Example 1 was compared with Comparative Example 2, it was seen that with an absorbent article comprising an absorber using only wood pulp as pulp, changing the single-layer absorber to an absorber with two stacked layers does not lower the rewetting amount of the absorbent article but rather increases it. When Comparative Example 1 was compared with Comparative Example 3, it was seen that even if a single-layer absorber using only non-wood pulp as the pulp is changed to an absorber with two stacked layers using non-wood pulp for the absorber on the front sheet side and using wood pulp for the absorber on the leakproof sheet side, the rewetting amount of the absorbent article is not lowered but is rather increased.

In Examples 1 and 2, the mean fiber size of ground pulp 4 used in the absorber on the front sheet side was 34.5 µm, while the mean fiber size of ground pulp 1 used in the absorber on the leakproof sheet side was 17.9 µm. Considering that the absorption capacity for fluids by capillary movement of the ground pulp is reduced if the mean fiber size is increased, it is expected that if ground pulp with a larger mean fiber size than the mean fiber size of the absorber on the leakproof sheet side is used for the absorber on the front sheet side, body fluid of a user will efficiently transfer from the absorber on the front sheet side to the absorber on the leakproof sheet side. This is thought to be the reason for the rapid absorption for 0.9% physiological saline in Examples 1 and 2. Conversely, if ground pulp with a smaller mean fiber size than the mean fiber size of the absorber on the leakproof sheet side is used in the absorber on the front sheet side, force may act to cause fluid to transfer from the absorber on the leakproof sheet side to the absorber on the front sheet side, thereby increasing the rewetting amount of the absorbent article, as seen with the rewetting amount of Comparative Example 3.

When Example 1 and Comparative Example 2 were compared, it was seen that when the amount of non-wood pulp in the absorber on the leakproof sheet side is reduced and the amount of wood pulp in the absorber on the front sheet side is increased, the rewetting amount of the absorbent article is greater.

EXPLANATION OF SYMBOLS 1, 31, 41 Absorbent article
2, 32, 42 Front sheet
3, 33, 43 Leakproof sheet
4, 34, 35, 45 Absorber
6, 36, 46 Tissue
21 Nylon mesh
22 Heat seal
24 Nylon mesh bag
37, 47 Second sheet

The invention claimed is:
1. An absorbent article, comprising:
   a layered absorber including first and second absorbers configured to absorb body fluids of a user and stacked in a thickness direction of the layered absorber,
   a liquid-permeable sheet covering one side of the layered absorber and permeable to the body fluids, and
   a liquid-impermeable sheet covering the other side of the layered absorber and impermeable to the body fluids,
wherein
   among the first and second absorbers,
      the first absorber on a side of the liquid-permeable sheet contains wood pulp obtained from needle bleached softwood kraft pulp, and
      the second absorber on a side of the liquid-impermeable sheet contains (i) non-wood pulp made from a portion near a core of Manila hemp or a portion between the core and a hull of Manila hemp, and (ii) a superabsorbent polymer,
   a mean fiber size of the non-wood pulp is 8 to 25 µm,
   the non-wood pulp has a hollow structure,
   a settling velocity of the non-wood pulp in water is between 2 seconds and 5 seconds, and a mean fiber size of the wood pulp is larger than the mean fiber size of the non-wood pulp.

2. The absorbent article according to claim 1, wherein
an apparent bulk density of the non-wood pulp is 0.04 to 0.07 g/cm$^3$, and
an absorption of the non-wood pulp for 0.9% physiological saline is at least 20 times the mass of the non-wood pulp.

3. The absorbent article according to claim 1, wherein the hollow structure of the non-wood pulp contains air.

* * * * *